United States Patent
Münzel et al.

(10) Patent No.: US 6,977,088 B2
(45) Date of Patent: Dec. 20, 2005

(54) METHOD FOR PEST CONTROL AND FOR PRODUCING LOW-CONCENTRATION PHOSPHINE AIR MIXTURES AND DEVICE FOR CARRYING OUT A METHOD OF THIS TYPE

(76) Inventors: Martin Münzel, Dr. Hans-Eisenmann-Strasse 19, 85354 Freising (DE); Rainer Schellhaas, Müllheimer Talstrasse 102, 69469 Weinheim (DE)

(*) Notice: Subject to any disclaimer, the term of this patent is extended or adjusted under 35 U.S.C. 154(b) by 58 days.

(21) Appl. No.: 10/220,091

(22) PCT Filed: Feb. 26, 2001

(86) PCT No.: PCT/EP01/02182

§ 371 (c)(1),
(2), (4) Date: Aug. 27, 2002

(87) PCT Pub. No.: WO01/64037

PCT Pub. Date: Sep. 7, 2001

(65) Prior Publication Data

US 2003/0021852 A1 Jan. 30, 2003

(30) Foreign Application Priority Data

Mar. 1, 2000 (DE) .................................. 100 09 888

(51) Int. Cl.[7] .............................................. A61K 33/42
(52) U.S. Cl. ...................................................... 424/601
(58) Field of Search ........................................ 424/601

(56) References Cited

U.S. PATENT DOCUMENTS

| | | | |
|---|---|---|---|
| 3,788,545 A | | 1/1974 | Budd et al. |
| 3,854,984 A | | 12/1974 | Klass et al. |
| 5,411,704 A | * | 5/1995 | Schellhaas et al. ........... 422/29 |
| 5,573,740 A | * | 11/1996 | Banks et al. ................. 423/299 |

FOREIGN PATENT DOCUMENTS

| | | |
|---|---|---|
| DE | 198 39 385 A1 | 3/2000 |
| EP | 0 783 896 | 7/1997 |
| EP | 0 981 960 A1 | 3/2000 |
| GB | 2 177 004 A | 1/1987 |
| GB | 2177004 | * 1/1987 |

OTHER PUBLICATIONS

"Schalldämpfung pneumatischer Ausrüstungen mit Schalldämpfem", in: Vyon, Wilhelm Köpp, Zellkautschuk GmbH & Co.

* cited by examiner

*Primary Examiner*—Alton Pryor
(74) *Attorney, Agent, or Firm*—Henry M. Feiereisen; Ursula B. Day

(57) ABSTRACT

In the control of pests in gas-tight spaces using gaseous phosphine, concentrated phosphine gas is passed through a phosphine-permeable dividing wall and then immediately combined with air to give phosphine-air mixtures with concentrations below self-ignition limits. Control of pests in gas-tight spaces comprises: (a) providing a source of phosphine (PH3) in concentrated form; (b) conducting the concentrated gaseous phosgene from the source into an air stream through a PH3-permeable dividing wall such that the introduced PH3 is immediately diluted at its point of introduction to below the concentration limits for self-ignition of PH3-air mixtures; and (c) introducing the resulting PH3-air mixture into the space to be fumigated. An Independent claim is also included for an apparatus for performing the method comprising a tube fitted in its central region with at least one gas inlet manifold having a porous or PH3-permeable dividing wall with a flat outlet area; the tube can be combined with inlet and outlet pipes for a pressurized air stream; and the manifold can be combined with a concentrated PH3 gas source.

7 Claims, 2 Drawing Sheets

METHOD FOR PEST CONTROL AND FOR PRODUCING LOW-CONCENTRATION PHOSPHINE AIR MIXTURES AND DEVICE FOR CARRYING OUT A METHOD OF THIS TYPE

BACKGROUND OF THE INVENTION

The invention relates to methods for controlling pests in sufficiently gas-tight spaces, particularly those, in which bulk goods (agricultural products and other goods susceptible to pest attack) are stored or were stored or are to be stored loosely or packed, e.g. in bags, and other goods, e.g. of wood, by utilising gaseous phosphine (phosphorous hydride, $PH_3$) as fumigant, as well as a device for carrying out a method of this type. In general form, the invention further relates to a process for direct production of low-concentration phosphine-air mixtures with phosphine concentrations of less than about 1.80 volume % (18.000 ppm).

It is known to rely on the biosidic properties of gaseous phosphine for controlling storage, stock and garden pests, particularly in the form of insects and rodents.

Originally, the procedure for controlling pests by fumigation of spaces in which goods, susceptible to pests attack, are stored, were stored or are to be stored, e.g. agricultural goods such as grain, utilised suitable solid metal phosphides, which release gaseous phosphine when coming into contact with moisture in the air. The metal phosphide containing preparations are, for example, introduced in the form of compressed bodies or in sachet type packaging, into which air moisture can enter and from which the gradually released phosphine can escape in very diluted form and subsequently its biosidic action can take place.

Due to various reasons, which includes the toxicity of the utilised metal phosphides, the exothermic reaction with the air moisture as well as problems of constant phosphine release in space and over time, these conventional methods exhibited however numerous disadvantages, which are further described in detail in the introductory sections of the following mentioned publications of the state of the art.

It has already been proposed, that phosphine is not applied in the form of solid forerunner compounds, but directly as gas. In this way, GB-A-2 177 004, and the corresponding South African Patent Application 864806, proposed that for fumigation a mixture of phosphine and an inert diluting gas are utilised, provided in finished form for application in pressure containers. The diluting gas is preferably carbon dioxide, and the phosphine part preferably is less than 3 volume % based on the diluting gas. This gas mixture is to be applied in such a way, that the mixture is introduced directly from the pressure container via a suitable conduit in the container or store-room, in which agricultural products, such as grains, are stored.

A considerable disadvantage with this method is that the phosphine is only provided in very diluted form, with the result that at the application point large quantities of pressure containers with the finished gas mixture have to be maintained. Furthermore, it is not guaranteed that with a simple introduction of a finished mixture of phosphine and inert gas, that the gas mixture is actually uniformly distributed in the goods to be treated and for an adequate time.

A further suggestion for fumigation by applying gaseous phosphine, is found in DE-A-37 07 453. In the mentioned disclosure, it is proposed that gaseous phosphine is discharged out of conventional steel bottles, after an inert gas, for example carbon dioxide, had previously been added. The inert gas should be added to the gaseous phosphine to prevent that ignitable phosphine-air mixtures are formed during discharge from the gas bottle. The application is to occur in such as way that after a conventional sealing of a building, large containers of a rodent construction etc., the gaseous phosphine, mixed with inert gas, is simply introduced via a pressure control/sensitive adjustment valve as well as distribution valves and hose-pipes from outside to the spaces to be fumigated (for example a building, a silo-cell, a ship-hold). It is assumed that the phosphine containing gas mixture distributes itself sufficiently in the space to be fumigated.

The method has the disadvantage, that the phosphine has to be provided as a pre-mixture with inert gas or that, besides a phosphine source in the form of a steel bottle, additionally a special inert gas source has to be provided. In any case, the method, in cases of fumigation of floor or bulk stores, for example grain storage, which are sealed from the environment by means of gas-tight folios, results in additionally added gas "inflating" the store, whereby again no uniform distribution of the phosphine in the to be treated agricultural goods is guaranteed. Additionally regarding the state of the art, reference is made to DE-A-36 08 256, DE-A-36 18 297 as well as DE-A-38 37 560, which are particularly concerned with the sealing of grain floor stores or bulk stores.

The older DE 198 39 385 A1, not disclosed before the priority date of the present invention, furthermore discloses a method, whereby in order to be able to work with concentrated phosphorous hydride, the latter is mixed with air and the resulting mixture is immediately thereafter, before discharge to the space to be fumigated, allowed to percolate through an aqueous liquid. In this manner no movement of concentrated phosphorous hydride directly into the air of the space to be fumigated occurs, because the position of the mixture production and the air space of the space to be fumigated are continuously separated by a water layer. However, under the water layer or before the discharge of the mixture in the water layer, ignitable mixtures can form. In any case, the flow speed of the air or the gas mixture is restricted, and an efficient circulation of the atmosphere of a fumigated room under enrichment with phosphorous hydride is not easily possible due to the water layer located in the flow route.

SUMMARY OF THE INVENTION

The present invention has as object, whilst preventing the disadvantages of the mentioned state of the art, to disclose a method for controlling pests in sufficiently gas-tight spaces and the goods if stored therein, by applying gaseous phosphine as fumigant, in which it is possible to work with substantially pure concentrated phosphine without additional preparation and/or introduction of inert gases, and by means of which a uniform distribution of the phosphines in the treated room is ensured, without mentionably increasing the quantity of gas in the treated space.

The present invention has as a further object, to disclose a suitable arrangement for carrying out a method of this type.

The mentioned object is solved in a general form by way of a method for controlling pests in sufficiently sealed spaces, in that a source for phosphine is presented that provides phosphine in concentrated form, that concentrated gaseous phosphine is introduced into an air stream from the phosphine source through a phosphine permeable dividing wall, so that the phosphine released through the separating wall is immediately diluted at the point of introduction to below the concentration limit for self-ignition of phosphine-air mixtures, and that the resulting diluted phosphine air mixture is introduced into the sufficiently sealed spaces and/or the bulk goods stored therein.

Advantageous embodiments of such a method are given in claims 1 to 3 and are further explained in the following detailed description of the invention.

According to a general aspect, the present invention relates furthermore to a method for producing low-concentration phosphine-air mixtures with phosphine concentration of less than about 1.80 volume %, in which a source for inert gas free phosphine is presented, the phosphine is provided in concentrated form, free of foreign gases, the concentrated gaseous phosphine is introduced into an air stream from the phosphine source through a phosphine permeable dividing wall, such that the introduced phosphine is immediately diluted at its point of introduction to below the concentration limit for self-ignition of phosphine-air mixtures, and that the resulting diluted phosphine-air mixture is then supplied to the intended end application.

A further aspect of the invention relates to an arrangement required for carrying out such a method and having features as given in claims 3 and 4.

The invention relates to the controlling pests by means of fumigation of "sufficiently sealed spaces" of any type. Under "sufficiently sealed" is to be understood spaces, which are on the one hand sealed so well that the required phosphine concentrations can be built up therein for adequately long periods, while on the other hand, no dangerous or unacceptable phosphine release to the environment of the sealed spaces results. The sealing requirements and the permissible measurable, phosphine concentration outside the fumigated spaces may vary according to the type and location of the fumigated spaces.

Accordingly, the spaces can also be buildings, parts of buildings, greenhouses, transport means and the like, which, due to their construction, are sufficiently gas-tight. Should this not be the case, then they have to be sealed by way of known methods for fumigation purposes. Gas-tight spaces can also be artificially acquired by way of known methods, e.g. bag piles, that have been gas-tightly packed.

The pests can also include stock pests, which occur in agricultural goods or in cultivated and processed agricultural products, or in the storage and production spaces to be treated, whereby e.g. also machines and pipes are included. The pests can also be hygienic, greenhouse, forestry or material pests, which reside in the gas-tight spaces to be fumigated or the materials and goods found therein. For simplification purposes, the invention is hereafter further explained with the focus on the example of controlling typical stock pests.

Thereby the fumigation occurs as fumigation of spaces in which agricultural products in the broadest sense are stored, normally as bulk goods, which can be stored loosely, which, however, can also occur in packaging units, e.g., bags, and which are endangered by pest attack. The goods can, for example, be stored harvested goods, e.g. grain and vegetables, however also their processed products e.g. grist, grain flour or corn flour. The goods can also be of animal origin or e.g. wood, e.g. for use as building material or components, or plants, particularly dried or those in a growth phase. Furthermore, the spaces to be fumigated can also be substantially empty or contain only residues of the goods contained therein, e.g. of those in which pests can occur. Besides stores for various agricultural goods, the spaces to be fumigated can also be factory halls, e.g. those of the food industry, or grain mills.

According to the present invention, the phosphine for the fumigation is applied directly from an inert gas free phosphine source. The phosphine source is preferably a conventional phosphine containing steel bottle, but can also be phosphine in concentrated form, i.e. with a concentration above the limit for self-ignition, or a supplying chemical phosphine generator. The phosphine can be applied in substantially pure, high concentrated form and—if required after a certain pre-purification of the mixture partner—mixed directly with the ambient air. This has the advantage, that only a minimum of gas containers, namely only one or more phosphine steel bottle(s), are to be provided at the application site. The phosphine contained in such a steel bottle need not be of high purified form, as required for example for application in the electronics industry and in chemical laboratories, but can also be provided in a less purified stage. When in the context of the present application there reference is made to the fact that the phosphine is applied in concentrated form or in inert gas free form, this does not exclude the presence of minor amounts of inert gas. The aim of the mentioned embodiments is merely to illustrate, that the phosphine can be applied without purposefully adding inert gas and during the production of phosphine-air mixtures without the intermediate special mixing with inert gases. The formed mixtures contain, besides the natural components of air and the phosphine, no additional process required inert gas components.

However, it follows for the person skilled in the art, that the method in accordance with the invention, when no pure phosphine is available, can also be performed with phosphine having inert gas parts, even if all the possible advantages of the invention cannot be acquired by performance of such method.

According to the method in accordance with the invention, the concentrated gaseous phosphine is introduced into an air stream from the phosphine source, so that the introduced phosphine is immediately taken up by the air stream at the point of introduction and is diluted to below the concentration limit for the self-ignition of phosphine-air mixtures. This is achieved in that the introduction of the phosphine into the air stream occurs through a phosphine permeable dividing layer, i.e. a dividing layer with fine pores or a dividing layer of a material through which gradual diffusion of phosphine is possible, so that a two-dimensional phosphine discharge area with only minor local phosphine concentration is obtained, whereby it is ensured that the boundary layer as well as the volume of phosphine-air mixtures with ignitable concentrations as well as the time of direct contact of the in-flowing phosphine into the boundary layer, is very small.

The phosphine permeable dividing layer, preferably in the form of a shape retaining dividing layer, can, regarding the material and/or the spatial form be constructed differently. However, as a rule is provided as a porous structure and/or contains a material, through which the phosphine can diffuse. The discharge of the phosphine into the air stream occurs under a minor pressure and at a rather low flow speed and possesses as a rule the character of a slow leakage. The air stream spreading over the planar discharge point of the dividing wall, immediately takes up the phosphine and ensures a rapid distribution.

In practice, various embodiments for the phosphine introduction into the air stream have proven to be suitable. A particularly advantageous introduction is achieved, when the air stream is allowed to flow through an open pipe, in which a thin phosphine introduction pipe is introduced from the side, whose end is closed off by means of a phosphine permeable dividing wall and has been bent rounded-off so that the phosphine is discharged substantially in the centre of the pipe. For the uniform planar distribution of the discharged phosphine, the phosphine introduction pipe is provided in a preferred embodiment form with a porous cap, which can, for example, be a commercial common sound absorber for pneumatic devices. Such sound absorbers are, for example, commercial products obtainable under the trade mark Vyon® (Wilhelm Köpp, Aachen). These are integral, porous shaped parts resembling closed rounded-off cylinders, which have been manufactured from a porous permeable plastics material. The mentioned commercial products are thereby produced by means of a synthetic process of low pressure polyethylene and are provided with a connecting component having a thread, which allows the direct connection to a pipe. When such sound absorbers are connected to pipes, the discharge sound of the pressure gas from a pipe conduit is reduced. In the context of the present invention, they ensure the desired phosphine discharge across a large surface in direct contact with the ambient air stream.

In place of a pipe conduit with a porous end-piece, for example in the form of the described sound absorber, the introduction of phosphine can also occur in that a hose is arranged in the air stream, particularly as a one-sided closed hose piece which consists of a material, which is permeable for diffusion of phosphine from the interior of the hose to the exterior. Also in this manner, a uniform, slow transport of phosphine into an airstream is ensured over a longer time period under controlled condition.

It is obviously in the context of the present invention, to combine in any described manner porous materials and such, through which phosphine can diffuse, e.g. to optimise the phosphine discharge amount and/or to modify the discharge surface. An example is the lining or surface coating of porous pipes with a material, through which phosphine can diffuse. The latter mentioned material thereby can be applied, e.g. also as a thin coating or painting on a more or less rigid porous substrate, and the porous substrate and coating together form the phosphine permeable dividing wall. The porous size can vary over a wide range in such cases, and the phosphine diffusion enabling material then need not be shape-retaining and can, e.g., also be provided as high viscose coating.

A particularly advantageous embodiment of the invention provides for the air stream, which takes up the phosphine moving through the phosphine permeable dividing wall, to be substantially formed by the air, which is sucked out of the space or bulk goods to be fumigated by using suitable suction devices, whereafter this air is led by means of a fan through the pipe, in which the air is enriched with phosphine, whereafter the phosphine-air mixture is returned over a corresponding suitable introduction arrangement again to the space to be fumigated. The suction or discharge devices can, for example, also be pipes or pipe lances introduced into the bulk goods at different points and at different depths. The combination of suction and introduction supports a uniform distribution of the phosphine-air mixture in the space or bulk goods to be fumigated, without that the introduction of the mentioned mixture of the gas volume is increased, so that the known inflation effect or the risk of an accidental, non-uniform phosphine concentration does not occur.

The method can also be performed as a continuous re-cycling method, as intermittently operating recycle process or also can be carried out in such a way, that the space to be fumigated is firstly saturated with phosphine-air mixture and is then left resting over a desired time period in gas-tight closed state.

It is advantageous with the method in accordance with the invention, when the air, particularly if it is taken from the treated goods, is purified from dust and additionally is subjected to a treatment for removal of reactive hydroxyl radicals. The removal of hydroxyl radicals can thereby take place by means of known methods, in that the air is led over or through a substrate soaked in a suitable reactive compound, whereby particularly those compounds come into consideration which are safe in view of contact with food, for example diethyl hydroxylamine. Insofar as allowed in special application cases, other compounds can also be used, e.g. aniline.

The phosphorous hydride is subjected, particularly then, when it is applied in a less highly purified form, to an additional purification for removal of di-phosphine and higher phosphines, which can occur by flowing through a tower packed with molecular sieves.

The utilized possibility in the context of the present invention, to produce low-concentration phosphine-air mixtures directly from concentrated phosphine gas, can also be used in simplified form for other technical application cases, in which phosphine-air mixtures are required. In accordance with the described technology, additionally to the phosphine or even instead of the phosphine, other easily ignitable gases or vapors can be mixed in low concentrations with air, for example by arranging a further point of introduction in the flow pipe or by connecting the point of introduction to another or further gas or vapour source.

BRIEF DESCRIPTION OF THE DRAWING

Hereafter the present invention is further explained with reference to three figures. In the figures there is shown in FIG. 1 a flow diagram of an embodiment of a plant for carrying out the method in accordance with the invention.

DETAILED DESCRIPTION OF THE PREFERRED EMBODIMENTS

Figure 1:
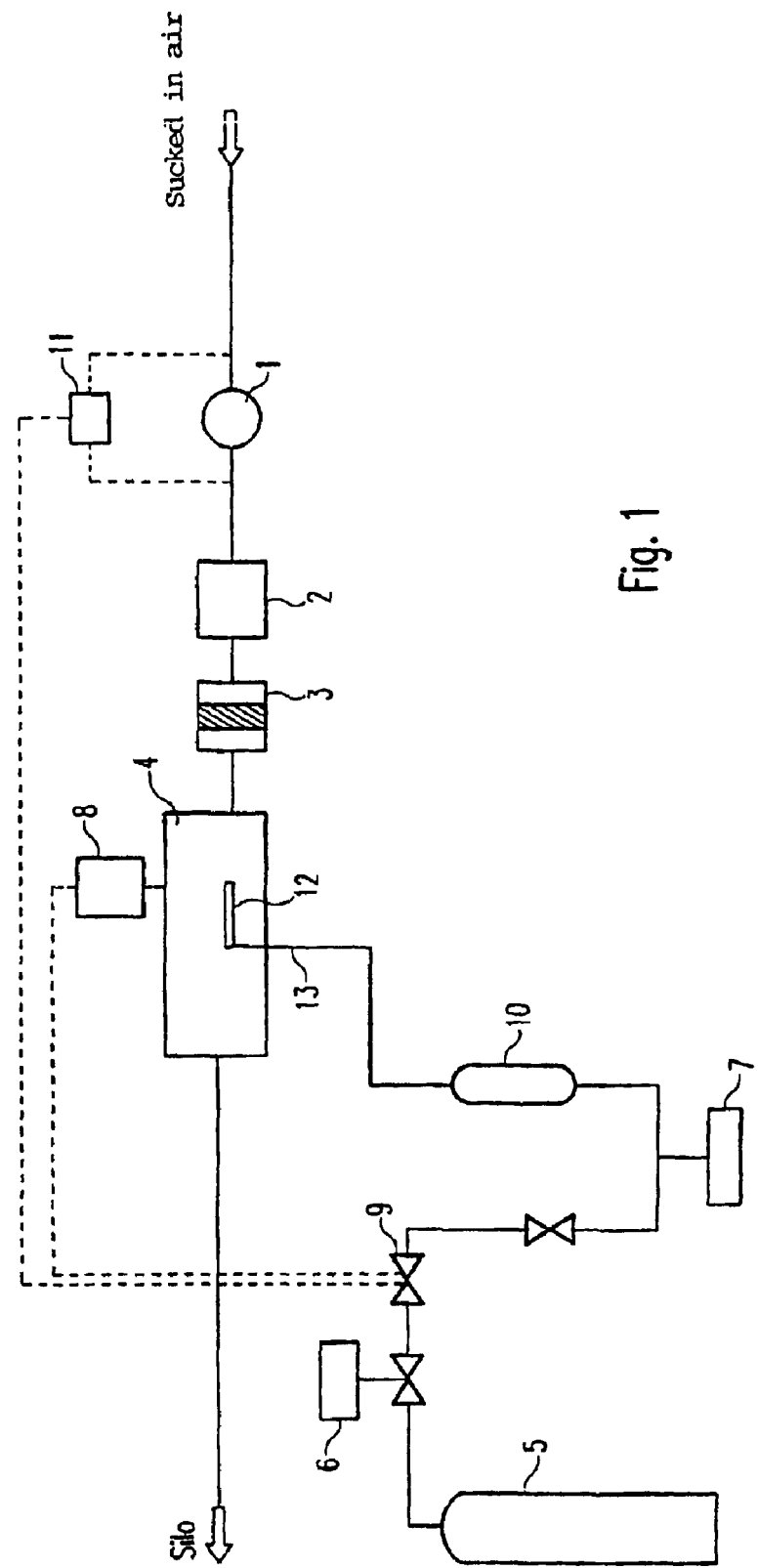

According to FIG. 1, a preferred embodiment for the method in accordance with the invention, is described as follows: from a fan 1 the air is sucked from the space to be fumigated or the hollow chambers of bulk goods or also from the ambient air through a dust filter 2 and then led through a suitable substrate 3, for example in the form of a flow-through fibre or particulate material, which has been soaked in aniline or diethylhydroxylamine, to reduce the concentration of hydroxyl radicals in the air. The air pre-purified in this manner is led to the pipe-shaped mixing chamber 4, where the desired amount of phosphine is added, which is obtained from a phosphine source 5, which provides phosphine in concentrated and in a form substantially free of foreign gas. The phosphine source is schematically shown in the figure as a gas pressure bottle 5 with a pressure control valve 6. The desired volume stream of the phosphine from the gas bottle is regulated by means of through-flow control 7. Before the introduction into the air stream, the phosphorous hydride is preferably led over a tower 10 filled with molecular sieves (Quality 5A), to retain diphosphine and higher phosphine. Thereafter the phosphine reaches the mixing chamber 4 and moves into the air stream, which flows through the mixing chamber 4.

The mixing chamber 4 is divided, in the embodiment form shown, with a security arrangement having the shape of a temperature difference indicator 8, which detects, for example, an ignition of the phosphine depending temperature change and operates a shutting device 9 in the context of a cut-off of the phosphine stream. A further security arrangement is the detection of the uniformity of the air volume stream, for example by pressure difference measurement by means of a pressure difference indicator 11 at the fan 1, and a disturbance decrease of the air stream volume also causes disruption of the phosphine supply.

Figure 2:
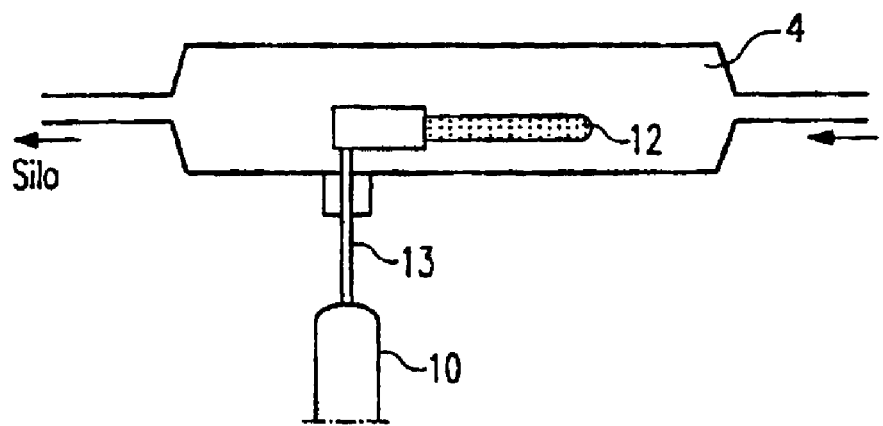
FIG. 2 a first embodiment of a mixing pipe with a phosphine conduit by using a porous element.

FIG. 2 shows schematically a first embodiment of a pipe-shaped mixing chamber 4, at which the phosphine introduction occurs through a porous dividing wall 12 with an expanded surface and axially arranged in the mixing chamber pipe, which here has the form of a substantially closed porous cylinder.

Figure 3:
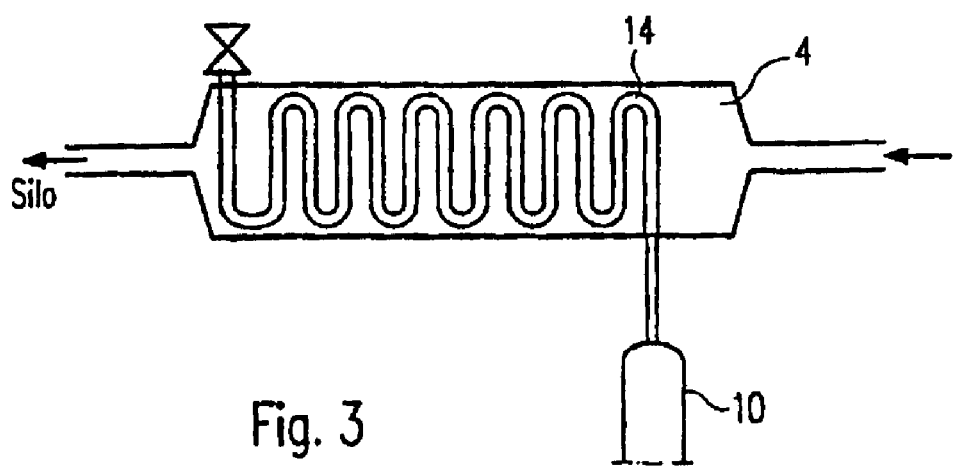
FIG. 3 an alternative of an embodiment form of a pipe-shaped mixing chamber, in which the phosphine diffuses through the wall of a hose into the air stream.

According to FIG. 3 the enrichment of the air stream with phosphine occurs in that phosphine diffuses from an one-sided closed hose 14 located in the air stream and of suitable length.

In the embodiment of the mixing chamber 4 shown in FIG. 2, the chamber is formed as a pipe, whose diameter is chosen depending on the desired air stream, whereby a minimum flow speed of the air stream of 10 m/s should be reached. The phosphine is added via a pipe 13 arranged through the wall of the chamber and exits through a porous dividing wall, which forms a suitably shaped discharge surface. The dividing wall can be a plate, a pipe or an element in the form of the described sound absorber. It obviously is possible, to arrange more than only one pipe 13 in the mixing chamber, and it is imaginable, for special applications and within the scope of the present invention, to provide additional introduction points for other gases or even easily ignitable components.

The alternative embodiment shown in FIG. 3 of the mixing chamber 4 consists of a channel in which a phosphorous hydride permeable hose 14 (for example a polyethylene hose) is arranged in such a way, that it is surrounded freely by the air stream. In this case the flow speed, due to the low discharging phosphine amount, can be low (<1 m/s). The hose is filled with phosphine, then enclosed on the one side and supplied from a phosphorous hydride source with phosphorous hydride. By means of diffusion the phosphorous hydride enters very slowly over a relatively large surface area and into the channel or into the air flowing past.

EXAMPLE

The example concerns the fumigation of a silo with 500 t of grain.

Dosage: 3 g $PH_3$ per ton

For fumigating 500 t grain by utilising 3 g $PH_3$ per ton, 1,500 g phosphine has to be introduced into the silo cell. If the upper concentration limit in the volume stream is 10,000 ppm (about 14 g/$m^3$), about 100 $m^3$ of air is required. If the mixing chamber has a diameter of 10 $cm^3$ and the air from the silo cell with a speed of 10 m/s is sucked in and led through the mixing chamber, then for 1 $m^3$ of air 100 seconds are required. To introduce the required 100 $m^3$ the time required thus is 10,000 sec or 2 h 46 min. Such a method variance is possible in practice, in that for example three suction pipes with cross-sectional areas of about 3.3 $cm^3$, which exhibit suitable suction openings protected against grain entering, for example sieves, are provided in the goods to be fumigated and sealed relative to the ambient air, and connected to the suction side of a fan. Air from the free air space or another suitable place of the sufficiently sealed space to be fumigated can also be sucked in.

The sucked-in air is then transported through the fan through the mixing chamber and after flowing through the mixing chamber and after subsequent enrichment by means of phosphine is introduced into the fumigated space or the bulk goods, in that for example corresponding pipes, as for suction, are also used for the introduction of the phosphine-air mixtures.

What is claimed is:

1. A method for controlling pests in sufficiently gas-tight spaces, using gaseous phosphine ($PH_3$) as fumigant, comprising:

delivering concentrated phosphine from a phosphine source, the phosphine source being a phosphine gas bottle having an exit valve;

connecting the exit valve to a closed conduit, the conduit having a phosphine permeable dividing wall;

interposing the phosphine permeable dividing wall within a stream of forced air;

filling said closed conduit with concentrated phosphine delivered from the gas bottle so that said concentrated phosphine is permeating through the phosphine permeable dividing wall such that the so permeated phosphine is immediately diluted upon contact with the forced air stream at a point of introduction to below a concentration limit for self-ignition of phosphine-air mixtures, and introducing a resulting diluted phosphine-air mixture into the space to be fumigated.

2. The method according to claim 1, wherein the phosphine permeates said phosphine permeable dividing wall by means of one of pores or by diffusion.

3. The method according to claim 1, wherein the phosphine permeable dividing wall is formed by an element selected from the group consisting of a porous sound absorber for pneumatic equipment, a porous pipe or hose and a pipe or hose from material permitting permeation of phosphine by diffusion.

4. The method according to claim 1, wherein the phosphine permeable dividing wall is located in a pipe-shaped mixing chamber through which a forced air stream is guided.

5. The method according to claim 1, wherein the forced air stream consists at least in part of air sucked in from the gas-tight spaces to be fumigated and wherein the air after enrichment with phosphine, is returned again to the spaces to be fumigated.

6. The method according to claim 1, wherein the sufficiently gas-tight spaces to be fumigated are those for storage of agricultural goods stored or closed grain floor stores or bulk stores.

7. The method according to claim 1, wherein prior to introduction into the forced air stream, the phosphine is subjected to a purification treatment for removal of diphosphine, and/or wherein the air stream is subjected to a purification treatment for removal of dust and/or hydroxyl-radicals.

* * * * *